United States Patent [19]

Aronsohn

[11] Patent Number: 4,608,370

[45] Date of Patent: Aug. 26, 1986

[54] SKIN FORMULATION

[76] Inventor: Richard B. Aronsohn, 10571 Wyton Dr., Los Angeles, Calif. 90024

[21] Appl. No.: 707,862

[22] Filed: Mar. 4, 1985

[51] Int. Cl.⁴ ............................................... A61K 7/48
[52] U.S. Cl. .............................. 514/159; 424/DIG. 2; 424/DIG. 4; 514/163; 514/557; 514/848; 514/859; 514/864
[58] Field of Search ...................... 514/557, 159, 163; 424/DIG. 4, 70, DIG. 2

[56] References Cited

U.S. PATENT DOCUMENTS

| | | | |
|---|---|---|---|
| 2,942,008 | 6/1960 | Lubowe | 424/DIG. 2 |
| 3,236,730 | 2/1966 | Galin | 424/146 |
| 3,265,571 | 8/1966 | Krezanoski | 424/157 X |
| 4,147,782 | 4/1979 | Klein et al. | 514/557 |
| 4,210,654 | 7/1980 | Bauer et al. | 424/DIG. 4 |
| 4,294,852 | 10/1981 | Wildnauer et al. | 514/29 X |
| 4,318,907 | 3/1982 | Kligman et al. | 514/859 |

OTHER PUBLICATIONS

Martindale, Extra Pharmacopoeia, 1958, vol. I, 24th edition, pp. 6 to 13, 1174 to 1183, 1278 and 1279.
Bennett, The Cosmetic Formulary, 1937, pp. 122, 233.

*Primary Examiner*—Dale R. Ore
*Attorney, Agent, or Firm*—Fraser and Bogucki

[57] ABSTRACT

Skin treating composition comprising about 3 to about 7 parts salicylic acid, about 8 to 12 parts resorcinol, about 8 to about 12 parts lactic acid, and about 60 to about 90 parts ethyl alcohol, by weight. The composition is applied to the face, and after approximately a week, causes light peeling of dead surface skin together with removal at least some blemishes, imparting a youthful and healthy complexion.

4 Claims, No Drawings

SKIN FORMULATION

BACKGROUND OF THE INVENTION

This invention relates to therapeutic skin treatment, and is particularly concerned with a skin care formulation and method for applying same particularly to the face, for imparting a youthful and healthy complexion.

Various compositions have been employed in the prior art for treatment of skin maladies including unsightly blemishes such as pimples and acne on the face.

Thus, for example, U.S. Pat. No. 3,265,571 discloses a formulation for the treatment of acne comprising salicylic acid, resorcinol and isopropyl alcohol. The patentee states that previously employed preparations for the treatment of such skin maladies in some instances contain 60% or more of alcohol as vehicles for salicylic acid, resorcinol and some anti-bacterial agents which could otherwise not be properly and adequately dispersed for dermatological use. However, it is noted that alcohol could increase the irritating effect where the skin is already highly inflamed.

U.S. Pat. No. 4,294,852 discloses a skin treating composition containing a combination of an acid such as lactic acid and an alcohol containing 4 to 6 carbon atoms, such as n-butanol.

U.S. Pat. No. 4,318,907 discloses a topical therapeutic composition for treating acne, containing salicylic acid and ethanol in aqueous solution, together with benzoyl peroxide.

U.S. Pat. No. 2,942,008 discloses an acne preparation comprising resorcinol monoacetate, salicylic acid and isopropyl alcohol.

U.S. Pat. No. 3,236,730 discloses dermatological preparations comprising salicylic acid and other components such as mercuric oxide and tetra sodium ethylene diamine tetra acetate.

However, none of the prior art, to applicant's knowledge, discloses a skin care formulation effective for cleaning and freshening the skin, and particularly when applied to the face, results in removal as by peeling, of dead skin, to impart a youthful and glowing complexion.

Accordingly, one object of the invention is the provision of a skin care formulation which is effective when applied to the skin to impart a fresh youthful appearance without any substantial irritating or astringent effect.

Another object is the provision of a therapeutic skin composition which is effective when applied to the face, to remove as by peeling, the dead skin layer, together with any unsightly blemishes, and a method for applying the skin composition for producing these desired results.

A still further object of the invention is the provision of a skin composition of the above type, employing several readily available therapeutic components, which when combined, particularly in certain proportions, and applied to the face, results in an improved fresh facial appearance.

SUMMARY OF THE INVENTION

The above objects and advantages are achieved, according to the invention, by the provision of a composition comprising as essential components, salicylic acid, resorcinol, lactic acid and ethyl alcohol, in certain effective amounts or ranges of proportions, as set forth in greater detail hereinafter.

The skin care composition of the invention is particularly effective when applied to the face for causing light peeling of dead surface skin, and imparting a youthful and healthy complexion.

The composition is used by applying it to the face, causing a "glowing" of the skin for a short period of time, and after a longer period of about a week or more, the outer dead skin layer is removed and disappears.

Other than for an initial light stinging effect lasting for a very short period of time, contact of the skin by the above composition does not result in any substantial irritating or harmful effect to the skin.

DETAILED DESCRIPTION OF THE INVENTION

One of the essential active ingredients or components of the skin treating composition of the invention is salicylic acid. It is in the form of a white powder and is effective as a therapeutic agent, and functions essentially as an antiseptic agent.

A second essential component of the composition is resorcinol which also functions as an effective therapeutic and antiseptic agent. This component is available as a white crystalline material.

A third essential component is lactic acid. This material also has antiseptic properties and is available in the form of a syrupy liquid.

The fourth essential component is ethyl alcohol which is effective as an antiseptic and also serves as a vehicle for the other three components noted above.

It has been found that the above components when combined in the ranges of proportions in the table noted below synergistically provide a skin treating composition which is particularly effective when applied to the face, to cause the epidermis to dry up and the resulting dead skin to peel off in a relatively short time of about a week or more, with the resulting skin exhibiting a fresh and youthful glow.

TABLE 1

| COMPONENTS | PARTS BY WEIGHT |
|---|---|
| Salicylic acid | 3–7 |
| Resorcinol | 8–12 |
| Lactic acid | 8–12 |
| Ethyl alcohol | 60–90 |

The composition is in the form of a liquid containing the resorcinol, salicylic acid and lactic acid in solution.

Exemplary specific skin treating compositions according to the invention are noted in Table 2 below.

TABLE 2

| | COMPOSITIONS (% BY WT.) | | |
|---|---|---|---|
| COMPONENTS | A | B | C |
| Salicylic acid | 5 | 4 | 6 |
| Resorcinol | 9.5 | 10 | 9 |
| Lactic acid | 9.5 | 11 | 8 |
| Ethyl alcohol | 76 | 75 | 77 |
| | 100 | 100 | 100 |

The following are examples of practice of the invention,

EXAMPLE I

The following formulation was prepared in the form of a solution of the components noted in the table below.

TABLE 3

| COMPONENTS | ozs. |
| --- | --- |
| Salicylic acid | 0.5 |
| Resorcinol | 1 |
| Lactic acid | 1 |
| Pure ethyl alcohol | 8 |
| | 10.5 |

It will be noted that the above composition corresponds to composition A of Table 2 above.

The composition or solution A above was applied by swabbing it on the face, creating a light stinging effect that lasts for two to three minutes. This changes to a "glow" lasting about two hours.

After a few days, typically a week, the dead skin layer peels off. Some if not all of the unsightly blemishes such as pimples and acne also disappear or are minimized. Lines and wrinkles are smoothed. There results the appearance of a youthful, glowing and healthy complexion.

EXAMPLE II

Skin compositions corresponding to Examples B and C of Table 2 above are also applied respectively, to the face by substantially the same procedure as noted in Example I above.

Substantially the same improved results in terms of improved and youthful facial appearance are obtained as in the case of Example I above.

It is noted that the improved results of Examples I and II above are obtained without any accompanying irritation or inflammation of the treated skin areas, except for the above noted light stinging effect felt for only a short period of time directly after the composition is applied to the topical facial areas.

From the foregoing, it is seen that the invention provides a unique skin treating composition consisting essentially of a combination of four readily available components, which when combined provides a composition which when applied to the face, effects light peeling and skin freshening, substantially without any deleterious side effects such as irritation or burning of the skin. In effect, the skin formulation of the invention functions to deaden the outer skin layer or epidermis, causing it to dry up and to peel off.

Since various changes and modifications of the invention will occur to and can be made readily by those skilled in the art without departing from the invention concept, the invention is not to be taken as limited except by the scope of the appended claims.

What is claimed is:

1. A face treating composition effective when applied to the face to cause the epidermis to dry up and producing light peeling of dead surface skin, without any substantial irritating effect to the skin, which consists essentially of about 3 to about 7 parts salicylic acid, about 8 to about 12 parts resorcinol, about 8 to about 12 parts lactic acid and about 60 to about 90 parts ethyl alcohol, by weight.

2. The composition as defined in claim 1, consisting essentially of about 5% salicylic acid, about 9.5% resorcinol, about 9.5% lactic acid and about 76% ethyl alcohol, by weight.

3. A method for face treatment which comprises applying to the face the composition of claim 1, causing the epidermis to dry up and producing light peeling of dead surface skin without any substantial irritating effect to the skin.

4. A method for treating the face to impart a youthful and healthy complexion, which comprises applying to the face the composition of claim 2, causing an initial skin glow, and thereafter peeling and removal of dead surface skin, without any substantial irritating effect to the skin.

* * * * *